United States Patent [19]

Tsukuma et al.

[11] Patent Number: 4,915,625
[45] Date of Patent: Apr. 10, 1990

[54] CERAMIC ORTHODONTIC BRACKET

[75] Inventors: Koji Tsukuma, Atsugi; Seiji Oda; Hirotoshi Haga, both of Kawasaki, all of Japan

[73] Assignee: Tosoh Corporation, Shinnanyo, Japan

[21] Appl. No.: 214,038

[22] Filed: Jun. 30, 1988

[30] Foreign Application Priority Data

Jul. 2, 1987 [JP] Japan ............................ 62-163907
Jun. 2, 1988 [JP] Japan ............................ 63-134483

[51] Int. Cl.⁴ ........................... A61C 3/00; A61C 7/00
[52] U.S. Cl. ........................................ 433/8; 501/103; 106/35
[58] Field of Search .................. 501/103; 264/65, 66; 433/8, 199.1, 201.1, 202.1, 212.1, 9; 106/35

[56] References Cited

U.S. PATENT DOCUMENTS 4,753,902  6/1988  Ketcham ........................ 501/87
4,758,541  7/1988  Tsukuma ....................... 501/103
4,774,041  9/1988  Tsukuma et al. ............... 264/56

Primary Examiner—Mark L. Bell
Assistant Examiner—Deborah Jones
Attorney, Agent, or Firm—Cushman, Darby & Cushman

[57] ABSTRACT

A ceramic orthodontic bracket having an unobtrusive color, is obtained by sintering a molded body of a powdery mixture composed of 2-15 mole % of yttrium oxide, 5-20 mole % of titanium dioxide and the balance of zirconia.

4 Claims, 1 Drawing Sheet

CERAMIC ORTHODONTIC BRACKET

BACKGROUND OF THE INVENTION

(1) Field of the Invention

The present invention relates to a ceramic orthodontic bracket having a good transparency and unobtrusive color, and a process for making the same.

(2) Description of the Related Art

As the material of an orthodontic bracket, stainless steel and plastic materials such as polycarbonate have been used. Furthermore, alumina ceramic materials have been recently used.

Stainless steel has been generally used for orthodontic brackets. Stainless steel has an excellent strength and machinability, but since it has a metallic luster, when a stainless steel orthodontic bracket is attached to a row of teeth, the bracket stands out conspicuously and spoils the appearance of the patient. From the viewpoint of eliminating this defect of spoilage of the appearance, a transparent plastic bracket is sometimes used. But this plastic bracket has a problem such that slip between the bracket and an orthodontic wire is poor and a satisfactory orthodontic effect cannot be attained. An alumina ceramic bracket has excellent rigidity and a good slip between the bracket and wire, but since the transparency is poor, when the bracket is set in the mouth, the problem of the visible soilage of the brackets still arises.

SUMMARY OF THE INVENTION

An object of the present invention is to eliminate the above-mentioned defect and provide a transparent ceramic bracket which has excellent strength and an unobtrusive color, has good slip to metal and results in a satisfactory orthodontic effect.

The present invention is characterized in that transparent zirconia ceramics containing $Y_2O_3$ and $TiO_2$ are used for an orthodontic bracket.

DESCRIPTION OF THE PREFERRED EMBODIMENTS

Figure 1:
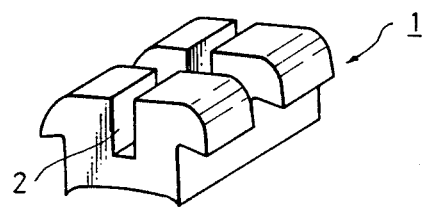
FIGS. 1 and 2 are diagrams illustrating the appearance of the orthodontic brackets of the present invention, as obtained in Examples 1 through 3.

In general, ceramics are opaque because of the scattering of light due to the presence of voids, grain boundaries and impurities. If these causes of scattering are drastically reduced, transparency can be imparted to the ceramics. The ceramics used in the present invention are a solid solution of yttria (a stabilizer)- and titania-doped zirconia. The addition of titania enables a high transparency to be imparted to zirconia ceramics, as disclosed in Japanese Patent Application No. 60-132,971 (Japanese Unexamined Patent Publication No. 62-91,467). The light-transmitting zirconia comprises 2 to 15 mole % of $Y_2O_3$ and 5 to 20 mole % of $TiO_2$, with the balance being $ZrO_2$. The highest light-transmitting property is attained in a composition comprising 6 to 8 mole % of $Y_2O_3$ and 10 to 15 mole % of $TiO_2$, with the balance being $ZrO_2$, and this ceramic has a fluorite type structure. The grain diameter of the sintered body is usually in the range of from 10 to 200 $\mu$m.

Preferably, the starting material is a fine powder having a high purity. For example, a fine powder obtained by adding hydrated titania obtained by hydrolyzing a titanium alkoxide to a powder of the $ZrO_2$-$Y_2O_3$ system having a grain diameter not larger than 0.3 $\mu$m and passing the mixture through blending, drying, sintering and pulverizing steps is preferably used as the starting material. The powder is molded and the molded body is sintered at a temperature of at least 1,300° C. preferably in an oxygen-containing atmosphere, and in order to attain a sufficient grain growth, preferably sintering is conducted at 1,600° to 1,800° C. To obtain transparency, the sintered body is preferably subjected to the hot isostatic pressing at a temperature of 1,400° to 1,700° C. in an inert gas atmosphere. However, if the hot isostatic pressing is conducted, the sintered body is reduced and blackened, and accordingly, the original color must be restored by oxidizing the sintered body at a temperature of 800° to 1,200° C. in air or oxygen.

Good transparency and a high mechanical strength are required for a bracket material. The light transmission of the transparent zirconia sintered body does not substantially depend on the grain size, and the light transmission of the transparent zirconia sintered body is 54 to 67% in the case of a grain diameter of 20 $\mu$m and 59 to 68% in the case of a grain diameter of 200 $\mu$m at a sample thickness of 1 mm. In contrast, the strength depends greatly on the particle size and is about 30 kgf/mm$^2$ in the case of a grain diameter of 20 $\mu$m and about 19 kgf/mm$^2$ in the case of a grain diameter of 200 $\mu$m (expressed in terms of the three-point bending strength). Accordingly, an optimum grain diameter of the sintered body as the bracket material is in the vicinity of 20 $\mu$m.

An orthodontic bracket is prepared by machining a sintered body or by forming a molded body having a bracket shape by injection molding or slip casting, removing the binder, sintering the molded body to obtain a sintered body having a bracket shape, and polishing the surface of the sintered body.

The color of the bracket material is important for the appearance because the bracket is attached in the mouth. Transparent zirconia usually has a very thin light yellow color resembling the color of teeth. The yellowish tint can be reduced by decreasing the content of iron as an impurity, to several ppm from scores of ppm.

The transparent zirconia bracket of the present invention has an excellent rigidity and has good slip to a metal wire, and therefore, a satisfactory orthodontic effect can be obtained. Moreover, the bracket of the present invention has a transparency and a color resembling the color of teeth, and thus is unobtrusive. Therefore, the mental state of a patient can be remarkably alleviated. Of course, the bracket is not corroded by saliva and is harmless to the human body.

EXAMPLE 1

A fine powder of the $TiO_2$-$Y_2O_3$-$ZrO_2$ system [$Y_2O_3/ZrO_2 = 8/92$ by mole, $TiO_2/(ZrO_2 + Y_2O_3) = 10/90$ by mole] was molded at 1,000 kgf/cm$^2$ into a plate, and the molded plate was sintered at 1,400° C. for 2 hours under a circulation of oxygen. The sintered body was subject to a hot isostatic pressing at 1,500° C. and 1,000 kgf/cm$^2$ for 30 minutes in argon. The treated body was charged in an electric furnace and heated at 1,000° C. to obtain a plate-shaped sintered body. The sintered body was processed into a shape of a bracket by the ultrasonic machining technique, and then subjected to a barrel polishing treatment to obtain a transparent zirconia orthodontic bracket.

The appearance of the so-obtained bracket is shown in FIG. 1. A groove 2 extending in the longitudinal direction in the bracket 1, shown in the drawings, is a groove for passing an orthodontic wire.

EXAMPLE 2

To 100 g of a fine powder of the $TiO_2$-$Y_2O_3$-$ZrO_2$ system [$Y_2O_3/ZrO_2 = 8/92$ by mole, $TiO_2/(ZrO_2 + Y_2O_3) = 10/90$ by mole] were added 1.2 g of a polycarboxylic acid type dispersant, 1.2 g of an acrylic emulsion binder, and 34 g of pure water, and the mixture was blended for 16 hours by zirconia balls in a nylon pot to form a slurry.

The slurry was cast in a gypsum mold prepared by using a bracket model. After completion of the molding, the molded body was removed from the gypsum mold and dried, and the binder was removed and the molded body sintered at 1,500° C. for 2 hours under a circulation of oxygen. The obtained sintered body was subjected to hot isostatic pressing at 1,400° C. and 1,500° C. kgf/cm$^2$ for 30 minutes in argon gas. Then, the treated body was charged in an electric furnace and heated at 1,000° C. to obtain a translucent sintered body having a shape of a bracket. The surface of the obtained sintered body was polished to obtain a transparent zirconia orthodontic bracket.

The appearance of the obtained product is shown in FIG. 1.

EXAMPLE 3

Figure 2:
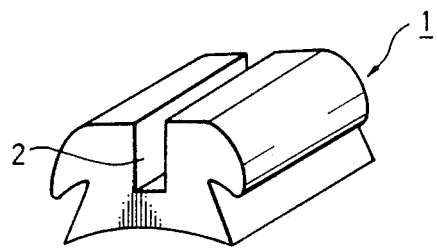

To 100 g of a fine powder of the $TiO_2$-$Y_2O_3$-$ZrO_2$ system [$Y_2O_3/ZrO_2 = 8/92$ by mole, $TiO_2/(ZrO_2 + Y_2O_3) = 10/90$ by mole] were added 4 g of an ethylene/vinyl acetate copolymer (UE633 supplied by Tosoh Corp.), 4 g of an acrylic rubber (PBMA CB-1 supplied by Sanyo Chem. Ind.), 6 g of paraffin wax, and 2 g of dibutyl phthalate (plasticizer), and the mixture was kneaded at 140° C. to prepare a material for injection molding. This starting material was injected at 160° C. into a mold having a shape of a bracket. Degreasing of the molded body was accomplished by heating the molded body to 800° C. at a temperature-evaluating rate of 5° C./hr, and sintering was accomplished by maintaining the molded body at 1,700° C. for 2 hours in an oxygen current. A transparent zirconia orthodontic bracket shown in FIG. 2, was obtained by polishing the sintered body.

I claim:

1. A ceramic orthodontic bracket having first and second faces, said first face having a shape appropriate for attachment to a tooth and said second face having wire support means, wherein said bracket is composed of a sintered body consisting essentially of 2 to 15% by mole of yttrium oxide ($Y_2O_3$), 5 to 20% by mole of titanium dioxide ($TiO_2$) and a balance of zirconia ($ZrO_2$).

2. The bracket according to claim 1, which is composed of a sintered body consisting essentially of 6 to 8% by mole of yttrium oxide, 10 to 15% by mole of titanium dioxide and the balance of zirconia.

3. A ceramic orthodontic bracket having first and second faces, said first face having a shape appropriate for attachment to a tooth and said second face having a longitudinal groove, wherein said bracket is composed of a sintered body consisting essentially of 2 to 15% by mole of yttrium oxide ($Y_2O_3$), 5 to 20% by mole of titanium dioxide ($TiO_2$) and a balance of zirconia ($ZrO_2$).

4. The bracket of claim 3, wherein said longitudinal groove comprises wire support means.

* * * * *